(12) United States Patent
Angwin et al.

(10) Patent No.: US 9,849,224 B2
(45) Date of Patent: Dec. 26, 2017

(54) VENTRICULAR ASSIST DEVICES

(71) Applicant: Thoratec Corporation, Pleasanton, CA (US)

(72) Inventors: Denise Angwin, Chelmsford, MA (US); Brian Kimball, Medford, MA (US); Christian Schade, Feldmeilen (CH); Patrick Kopson, Billerica, MA (US)

(73) Assignee: TC1 LLC, St. Paul, MN (US)

( * ) Notice: Subject to any disclaimer, the term of this patent is extended or adjusted under 35 U.S.C. 154(b) by 0 days.

(21) Appl. No.: 14/687,655

(22) Filed: Apr. 15, 2015

(65) Prior Publication Data

US 2015/0290375 A1     Oct. 15, 2015

Related U.S. Application Data

(60) Provisional application No. 61/979,811, filed on Apr. 15, 2014, provisional application No. 62/025,414, filed on Jul. 16, 2014.

(51) Int. Cl.
*A61N 1/362* (2006.01)
*A61M 1/10* (2006.01)
*A61M 1/12* (2006.01)

(52) U.S. Cl.
CPC ........ *A61M 1/1086* (2013.01); *A61M 1/1029* (2014.02); *A61M 1/122* (2014.02); *A61M 1/127* (2013.01); *A61M 2205/04* (2013.01); *A61M 2205/3334* (2013.01); *A61M 2205/3523* (2013.01); *A61M 2205/52* (2013.01); *A61M 2230/207* (2013.01)

(58) Field of Classification Search
CPC .... A61M 1/1086; A61M 1/122; A61M 1/127; A61M 1/1029; A61M 1/101; A61M 1/1005; A61M 1/10; A61M 2205/3334; A61M 2205/3523; A61M 2205/04; A61M 2205/52; A61M 2205/80; A61M 2230/207
See application file for complete search history.

(56) References Cited

U.S. PATENT DOCUMENTS

| | | | |
|---|---|---|---|
| 5,695,471 A | 12/1997 | Wampler et al. |
| 5,708,346 A | 1/1998 | Schoeb |
| 5,725,357 A | 3/1998 | Nakazeki et al. |
| 5,888,242 A | 3/1999 | Antaki |
| 5,947,703 A | 9/1999 | Nojiri et al. |

(Continued)

FOREIGN PATENT DOCUMENTS

| | | |
|---|---|---|
| EP | 1486217 A1 | 12/2004 |
| WO | 2003015609 A2 | 2/2003 |

(Continued)

*Primary Examiner* — Mallika D Fairchild
(74) *Attorney, Agent, or Firm* — Kilpatrick, Townsend & Stockton, LLP

(57) ABSTRACT

An implantable blood pump includes a control unit storing patient specific settings. The control unit is configured to store patient specific settings. The patient specific settings can be used to determine a target operating speed for the blood pump and/or a target operating mode for the blood pump. The patient specific settings can include at least one of an operating mode for the pump, a set speed for the pump, a lower speed limit for the pump, a patient hematocrit value, a patient hematocrit date, a patient blood density, and a periodic log rate for event and periodic data.

26 Claims, 5 Drawing Sheets

(56) References Cited

U.S. PATENT DOCUMENTS

| | | | |
|---|---|---|---|
| 6,053,705 A | 4/2000 | Schoeb et al. |
| 6,071,093 A | 6/2000 | Hart et al. |
| 6,100,618 A | 8/2000 | Schoeb et al. |
| 6,116,862 A | 9/2000 | Guenter et al. |
| 6,146,325 A | 11/2000 | Lewis et al. |
| 6,186,665 B1 | 2/2001 | Maher |
| 6,222,290 B1 | 4/2001 | Schöb et al. |
| 6,234,772 B1 | 5/2001 | Wampler |
| 6,249,067 B1 | 6/2001 | Schob et al. |
| 6,264,635 B1 | 7/2001 | Wampler |
| 6,278,251 B1 | 8/2001 | Schöb |
| 6,351,048 B1 | 2/2002 | Schob et al. |
| 6,355,998 B1 | 3/2002 | Schob et al. |
| 6,468,041 B2 | 10/2002 | Ozaki |
| 6,575,717 B2 | 6/2003 | Ozaki et al. |
| 6,589,030 B2 | 7/2003 | Ozaki |
| 6,605,032 B2 | 8/2003 | Benkowski et al. |
| 6,626,644 B2 | 9/2003 | Ozaki |
| 6,634,224 B1 | 10/2003 | Schöb et al. |
| 6,688,861 B2 | 2/2004 | Wampler |
| 6,707,200 B2 | 3/2004 | Carroll et al. |
| 6,817,836 B2 | 11/2004 | Nose et al. |
| 6,879,074 B2 | 4/2005 | Amrhein et al. |
| 6,949,066 B2 | 9/2005 | Bearnson et al. |
| 6,991,595 B2 | 1/2006 | Burke et al. |
| 7,112,903 B1 | 9/2006 | Schob |
| 7,138,776 B1 | 11/2006 | Gauthier et al. |
| 7,150,711 B2 | 12/2006 | Nüsser et al. |
| 7,229,474 B2 | 6/2007 | Hoffmann et al. |
| 7,239,098 B2 | 7/2007 | Masino |
| 7,284,956 B2 | 10/2007 | Nose et al. |
| 7,462,019 B1 | 12/2008 | Allarie et al. |
| 7,497,116 B2 | 3/2009 | Miyakoshi et al. |
| 7,511,443 B2 | 3/2009 | Townsend et al. |
| 7,520,850 B2 | 4/2009 | Brockway et al. |
| 7,591,777 B2 | 9/2009 | LaRose et al. |
| 7,645,225 B2 | 1/2010 | Medvedev et al. |
| 7,699,586 B2 | 4/2010 | LaRose et al. |
| 7,699,588 B2 | 4/2010 | Mendler |
| 7,854,631 B2 | 12/2010 | Townsendl et al. |
| 7,861,582 B2 | 1/2011 | Miyakoshi et al. |
| 7,887,479 B2 | 2/2011 | LaRose et al. |
| 7,951,062 B2 | 5/2011 | Morello |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,152,493 B2 | 4/2012 | LaRose et al. |
| 8,157,720 B2 | 4/2012 | Marseille et al. |
| 8,177,838 B2 | 5/2012 | Vodermayer et al. |
| 8,303,482 B2 | 11/2012 | Schima et al. |
| 8,323,174 B2 | 12/2012 | Jeevanandam |
| 8,382,830 B2 | 2/2013 | Maher et al. |
| 8,449,444 B2 | 5/2013 | Poirier et al. |
| 8,506,470 B2 | 8/2013 | LaRose et al. |
| 8,506,471 B2 | 8/2013 | Bourque et al. |
| 8,517,699 B2 | 8/2013 | Horvath |
| 8,556,795 B2 | 10/2013 | Bolyard et al. |
| 8,562,508 B2 | 10/2013 | Dague et al. |
| 8,597,350 B2 | 12/2013 | Rudser et al. |
| 8,652,024 B1 | 2/2014 | Masamichi et al. |
| 8,657,733 B2 | 2/2014 | Ayre et al. |
| 8,668,473 B2 | 3/2014 | LaRose et al. |
| 8,764,621 B2 | 7/2014 | Badstibner et al. |
| 8,870,739 B2 | 10/2014 | LaRose et al. |
| 8,882,477 B2 | 11/2014 | Fritz, IV et al. |
| 8,956,275 B2 | 2/2015 | Bolyard et al. |
| 2002/0123672 A1* | 9/2002 | Christophersom A61N 1/37282 600/300 |
| 2004/0152944 A1 | 8/2004 | Medvedev et al. |
| 2004/0230246 A1* | 11/2004 | Stein ............... A61N 1/08 607/32 |
| 2005/0071001 A1 | 3/2005 | Jarvik et al. |
| 2005/0187594 A1 | 8/2005 | Hatlestad et al. |
| 2007/0078293 A1 | 4/2007 | Shambaugh et al. |
| 2007/0119246 A1* | 5/2007 | Miyakoshi ......... A61M 1/101 73/168 |
| 2008/0021394 A1 | 1/2008 | LaRose et al. |
| 2008/0129517 A1* | 6/2008 | Crosby ............. A61M 1/10 340/573.1 |
| 2009/0203957 A1 | 8/2009 | LaRose et al. |
| 2010/0125316 A1* | 5/2010 | Marnfeldt ......... H04J 3/0638 607/60 |
| 2010/0130809 A1 | 5/2010 | Morello |
| 2010/0241223 A1 | 9/2010 | Lee et al. |
| 2010/0327687 A1 | 12/2010 | Iannello et al. |
| 2011/0015465 A1* | 1/2011 | Ayre ............... A61M 1/101 600/17 |
| 2011/0071337 A1 | 3/2011 | Thompson et al. |
| 2011/0160516 A1* | 6/2011 | Dague ............. A61M 1/12 600/16 |
| 2011/0237863 A1 | 9/2011 | Ricci et al. |
| 2011/0313237 A1 | 12/2011 | Miyakoshi et al. |
| 2012/0046514 A1 | 2/2012 | Bourque et al. |
| 2012/0078031 A1* | 3/2012 | Burke ............. A61M 1/122 600/16 |
| 2012/0095281 A1 | 4/2012 | Reichenbach et al. |
| 2012/0226097 A1 | 9/2012 | Smith et al. |
| 2012/0245681 A1 | 9/2012 | Casas et al. |
| 2013/0096364 A1 | 4/2013 | Reichenbach et al. |
| 2013/0121821 A1 | 5/2013 | Osaki et al. |
| 2013/0127253 A1 | 5/2013 | Stark et al. |
| 2013/0170970 A1 | 7/2013 | Osaki et al. |
| 2013/0225909 A1 | 8/2013 | Dormanen et al. |
| 2013/0289334 A1* | 10/2013 | Badstibner ....... A61M 1/127 600/16 |
| 2013/0314047 A1 | 11/2013 | Eagle et al. |
| 2013/0331934 A1 | 12/2013 | Kabir et al. |
| 2014/0100413 A1 | 4/2014 | Casas et al. |
| 2014/0194985 A1 | 7/2014 | Vadala, Jr. |
| 2014/0275723 A1 | 9/2014 | Fritz, IV et al. |
| 2014/0303426 A1 | 10/2014 | Kerkhoffs et al. |
| 2014/0357937 A1 | 12/2014 | Reyes et al. |
| 2015/0051438 A1 | 2/2015 | Taskin |

FOREIGN PATENT DOCUMENTS

| | | |
|---|---|---|
| WO | 201009287 A1 | 9/2010 |
| WO | 2012040544 A1 | 3/2012 |
| WO | 2014015300 A1 | 1/2014 |

\* cited by examiner

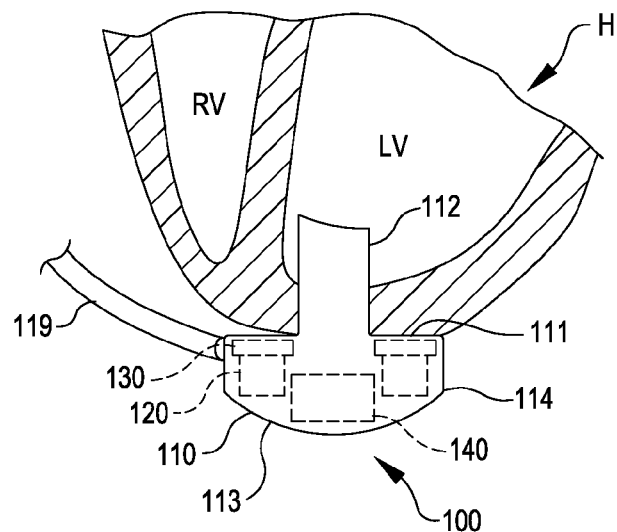
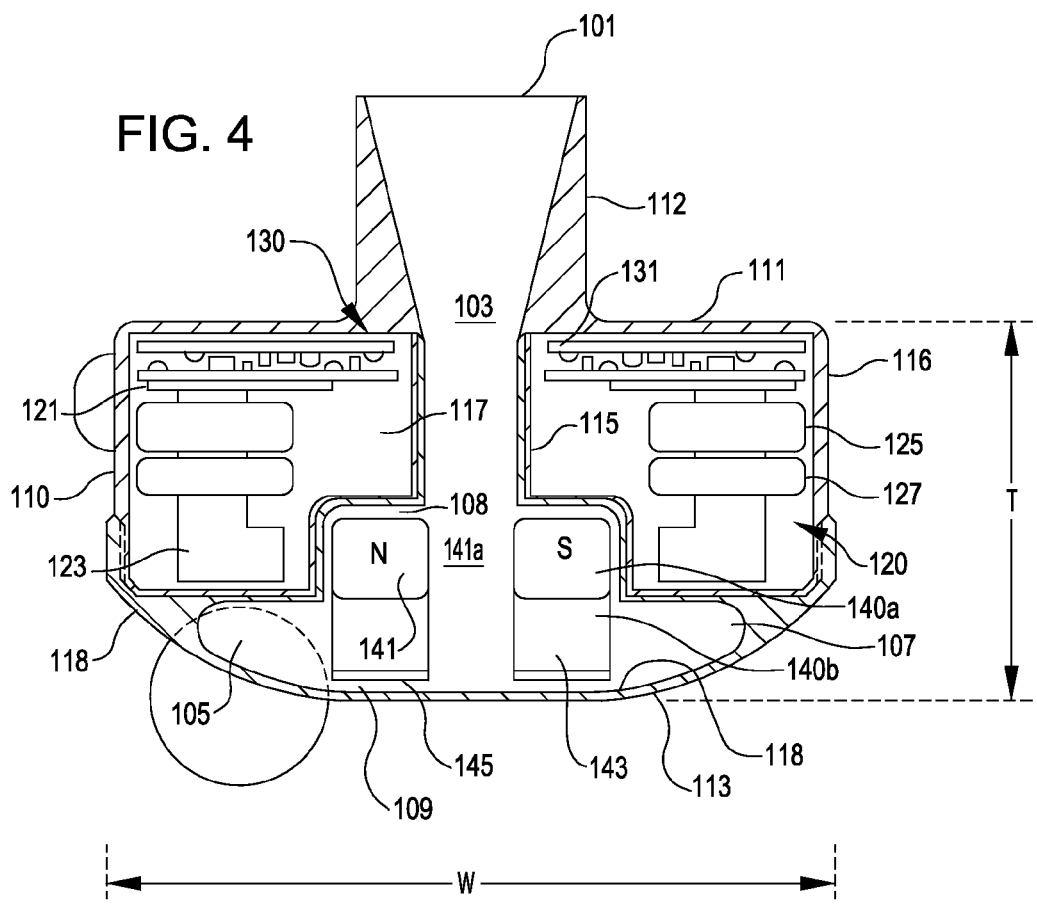

FIG. 7
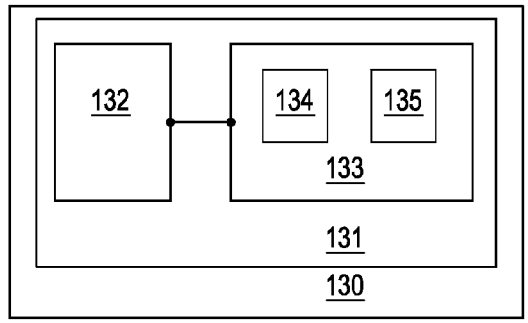
FIG. 8
- Set speed for blood pump
- Low speed limit for blood pump
- Operating mode for blood pump
- Hematocrit value
- Hematocrit date
- Blood density
- Log rate for event and periodic data
- Spoken language
FIG. 9
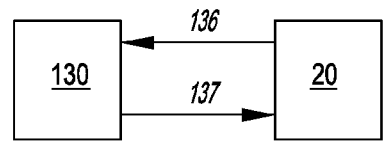
FIG. 10
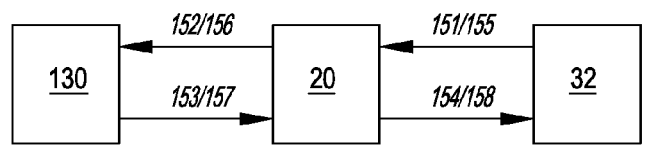

FIG. 11

| Target running mode for blood pump is set as stopped |
|---|
| Blood pump has just started up |
| Suction event is occurring |
| Instability of a rotor of the blood pump is occurring |
| Critical power hazard active for more than a predeterminded time |
| Blood pump is running on an emergency backup battery |
| Voltage of a backup battery less than a predetermined value |

FIG. 12

| Target running mode for blood pump is set as stopped |
|---|
| Current speed of the blood pump is less than an autostart threshold speed |
| Blood pump assembly is running on emergency backup battery power |
| Critical power hazard active for more than a predetermined time |

VENTRICULAR ASSIST DEVICES

CROSS-REFERENCE TO RELATED APPLICATIONS

This application claims the benefit of U.S. Provisional Application No. 61/979,811, filed Apr. 15, 2014 and also claims the benefit of U.S. Provisional Application No. 62/025,414, filed Jul. 16, 2014, both of which are incorporated herein by reference in their entirety for all purposes.

BACKGROUND

This application relates generally to mechanical circulatory support systems, and more specifically relates to an implantable control unit storing patient specific settings for an implantable blood pump.

Ventricular assist devices, known as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

An external non-implanted controller can be used to control operation of the implanted VAD. The external controller can be operatively connected to the VAD via a wired and/or mechanical connection. The connection can be used to supply the VAD with operating power (e.g., electrical and/or mechanical power) and control signals to control the operation of the VAD.

Such connections, however, may be less than optimal for the patient due to routing of the connection between the external controller, through the patient's skin, and to the implanted VAD. Accordingly, improved approaches and systems for controlling and/or powering a VAD are desirable.

BRIEF SUMMARY

As VAD systems continue to develop, the prevalence of implantable technologies such as electronics continues to rise in its implementation in such systems. The present invention provides new systems, methods, and devices which can advantageously allow for patient specific settings to be stored in implantable electronics associated with the VAD. Storing patient specific settings in implantable electronics within the patient has many practical and patient safety advantages as discussed below. For example, other components of the VAD system (e.g., external controller) may be exchanged without having to re-program the patient specific settings as they are stored in the patient. Still further, the patient specific settings may be changed or updated non-invasively or minimally invasively and without explantation, which results in less patient discomfort and lower costs. These updates may be transmitted via a hardwire or cable, or wirelessly.

Methods and systems for controlling an implantable blood pump assembly include storing patient specific settings in the blood pump assembly. For example, an implantable blood pump assembly can include an implantable control unit that stores the patient specific settings, which are used to control operation of the blood pump assembly. Storing the patient specific settings within the implanted blood pump assembly provides increased flexibility with regard to configuring a mechanical circulatory support system. For example, a VAD assembly storing patient specific settings in combination with a transcutaneous energy transfer system (TETS) may reduce the size of, and possibly even eliminate the need for, a skin-penetrating hard wire connection between the implantable blood pump assembly and an external controller. Additionally, a VAD assembly storing patient specific settings enables increased flexibility with respect to replacement of an associated external non-implantable external control unit because the VAD can continue to operate uninterrupted in accordance with the locally stored patient specific settings while the external control unit is being replaced.

Thus, in one aspect, an implantable blood pump assembly is provided. The an implantable blood pump and an implantable control unit communicatively coupled with the blood pump. The blood pump is configured to supplement or replace the pumping function of a heart. The control unit stores patient specific settings stored within the control unit. In many embodiments, the control unit is integrally housed with the blood pump. Alternatively, the control unit may be located in a separate implantable housing than the blood pump housing. For example, a system controller can be located in an implantable housing, and the control unit can be co-located in that same implantable housing in a fully implantable transcutaneous energy transfer system.

The patient specific settings stored within the implantable blood pump assembly are used to control one or more operational aspects of the blood pump. For example, the patient specific settings can include a patient specific operating mode of the blood pump. In many embodiments, the patient specific operating mode for the blood pump can be selected to be continuous or pulse. An external control unit can control the blood pump to run in a target operating mode selected as either the patient specific operating mode or continuous. The patient specific settings can include a patient specific set speed of the blood pump. The patient specific settings can include a patient specific low speed limit of the blood pump. The patient specific settings can include at least one of a patient specific hematocrit and a patient specific hematocrit date. The patient specific settings can include a patient specific blood density. The patient specific settings can include a patient specific periodic log rate for event and periodic data. And the patient specific settings can include a patient specific spoken language.

In many embodiments, the blood pump is controlled to run at a target speed. For example, the target speed can be based at least in part on at least one of a patient specific low speed limit of the blood pump and a patient specific set speed limit of the blood pump.

In many embodiments, the patient specific settings stored within the implantable blood pump assembly are the controlling settings that are used by one or more other systems in processing performed by the respective system. For example, the patient specific settings stored within the control unit are communicated to an external non-implanted controller for use in processing performed by the external controller. One or more of the patient specific settings stored within the control unit, however, can be selectively changed while the control unit remains implanted. For example, a medical professional can selectively change one or more of the patient specific settings, via, for example, an associated external non-implanted controller.

The implantable blood pump assembly can include suitable components for supplying operating power to the blood pump assembly. For example, the blood pump assembly can include a hard wire driveline to provide operating power to the pump assembly. As another example, the blood pump assembly can include a transcutaneous energy transfer system configured to provide operating power to the pump assembly.

In another aspect, a method of controlling an implantable blood pump assembly is provided. The method includes storing patient specific settings within an implantable control unit included as part of the implantable blood pump assembly and operating the blood pump in accordance with the patient specific settings stored within the implantable control unit. The patient specific settings include at least one of (a) a patient specific operating mode of the blood pump, (b) a patient specific set speed of the blood pump, (c) a patient specific low speed limit of the blood pump, (d) a patient specific hematocrit, (e) a patient specific hematocrit date, (f) a patient specific blood density, and (g) a patient specific periodic log rate for event and periodic data.

In many embodiments, the implantable pump is controlled to operate at a target speed that is based on at least one of the patient specific set speed, the patient specific low speed limit, and a set of event based rules for the target speed. The set of event based rules for the target speed can be based on at least one of the following events: (a) a target running mode for the implantable blood pump is set as stopped; (b) the implantable blood pump has just started up; (c) a suction event is occurring; (d) instability of a rotor of the implantable blood pump is occurring; (e) a critical power hazard has been active for more than a predetermined period of time; (f) the implantable blood pump is running on an emergency backup battery; and (g) voltage of a backup battery is less than a predetermined value.

In many embodiments, the implantable pump is controlled to operate in a target operating mode that is based on at least one of the patient specific operating mode of the blood pump and a set of event based rules for the target operating mode. The set of event based rules for the target operating mode can be based on at least one of the following events: (a) a target running mode for the implantable blood pump is set as stopped; (b) a current set speed for the implantable blood pump is set to be an auto-start threshold speed; (c) the controller is running on an emergency backup battery; and (d) a critical power hazard is active.

In many embodiments, the patient specific settings stored within the implantable control unit are used by all other related subsystems in any related processing. To facilitate such use, the method can further include transmitting the patient specific settings stored within the implantable control unit to a non-implanted external control unit.

The patient specific settings stored within the implantable control unit can, however, be changed, for example, by a medical professional in view of changed patient circumstances. Accordingly, the method can further include changing at least one of the patient specific settings stored within the implantable control unit while the implantable control unit remains implanted.

Because operational parameters for the implantable blood pump are stored in the associated implantable control unit, increase flexibility for replacing an associated non-implanted external control unit is provided. Accordingly, the method can include the following acts: (a) transmitting at least one of the patient specific settings from the blood pump assembly to a first external non-implanted controller for use in processing performed by the first external controller; (b) replacing the first external controller with a second non-implanted controller; the second external controller being different from the first external controller; and (c) transmitting at least one of the patient specific settings from the blood pump assembly to the second external non-implanted controller for use in processing performed by the second external controller.

BRIEF DESCRIPTION OF THE DRAWINGS

FIG. 3 is an illustration of a blood pump in an operational position implanted in a patient's body.

FIG. 4 is a cross-sectional view of the blood pump of FIG. 3.

FIG. 7 is a simplified schematic diagram of control electronics included within an implantable blood pump assembly, in accordance with many embodiments.

FIG. 8 shows patient specific settings that can be used in operational control of an implantable blood pump assembly, in accordance with many embodiments.

FIG. 9 is a simplified schematic diagram of communication of patient specific settings in a mechanical circulatory support system, in accordance with many embodiments.

FIG. 10 is a simplified schematic diagram of communication in a mechanical circulatory support system for changing patient specific settings stored in an implantable blood pump, in accordance with many embodiments.

FIG. 11 shows events that can be considered in event based rules for determining a target operating speed for an implantable blood pump assembly, in accordance with many embodiments.

FIG. 12 shows events that can be considered in event based rules for determining a target operating mode for an implantable blood pump assembly, in accordance with many embodiments.

DETAILED DESCRIPTION

Figure 1:
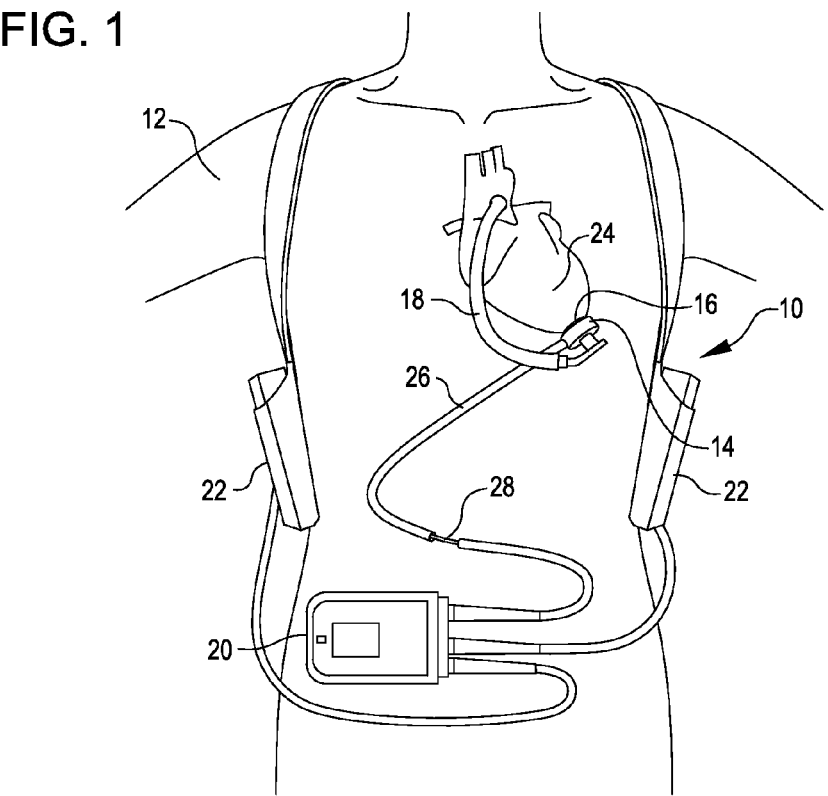
FIG. 1 is an illustration of a mechanical circulatory support system implanted in a patient's body.
Figure 2:
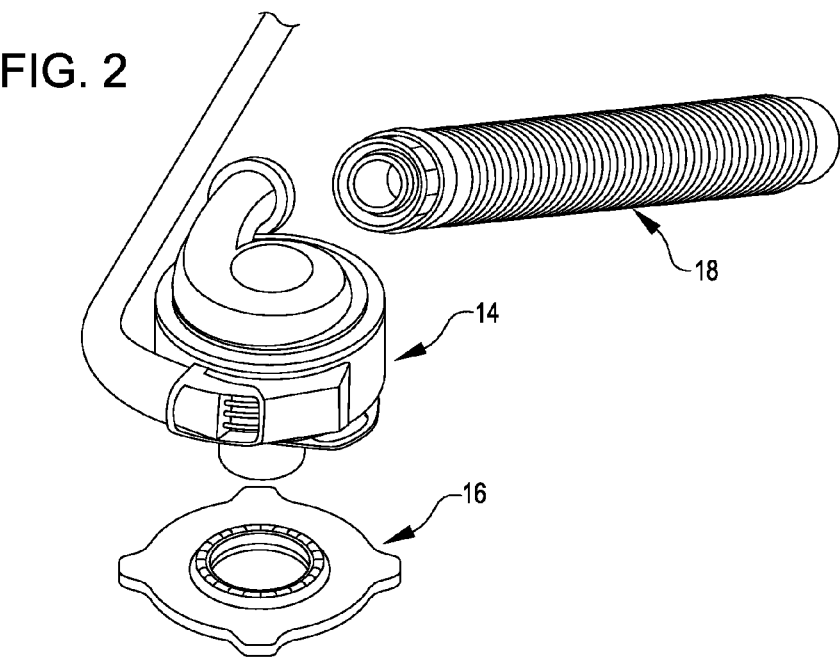
FIG. 2 is an exploded view of certain components of the circulatory support system that are implanted in a patient's body.

FIG. 1 is an illustration of a mechanical circulatory support system 10 implanted in a patient's body 12. The mechanical circulatory support system 10 comprises a implantable blood pump assembly 14, ventricular cuff 16, outflow cannula 18, an external system controller 20, and power sources 22. The implantable blood pump assembly 14 may comprise a VAD that is attached to an apex of the left ventricle, as illustrated, or the right ventricle, or both ventricles of the heart 24. The VAD may comprise a centrifugal (as shown) or axial flow pump as described in further detail herein that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety. With reference to FIGS. 1 and 2, the blood pump assembly 14 may be attached to the heart 24 via the ventricular cuff 16 which is sewn to the heart 24 and coupled to the blood pump 14. The other end of the blood pump 14 connects to the ascending aorta via the outflow cannula 18 so that the VAD effectively diverts blood from the weakened ventricle and propels it to the aorta for circulation to the rest of the patient's vascular system.

FIG. 1 illustrates the mechanical circulatory support system 10 during battery 22 powered operation. A driveline 26 that exits through the patient's abdomen 28, connects the implanted blood pump assembly 14 to the external system controller 20, which monitors system 10 operation. Related controller systems applicable to the present invention are described in greater detail below and in U.S. Pat. Nos. 5,888,242, 6,991,595, 8,323,174, 8,449,444, 8,506,471, 8,597,350, and 8,657,733 and U.S. Patent Publication Nos. 2005/0071001 and 2013/0314047, all of which are incorporated herein by reference for all purposes in their entirety. The system may be powered by either one, two, or more batteries 22. It will be appreciated that although the system controller 20 and power source 22 are illustrated outside/external to the patient body, the driveline 26, system controller 20 and/or power source 22 may be partially or fully implantable within the patient, as separate components or integrated with the blood pump assembly 14. Examples of such modifications are further described in U.S. Pat. No. 8,562,508 and U.S. Patent Publication No. 2013/0127253, all of which are incorporated herein by reference for all purposes in their entirety.

Figure 5:
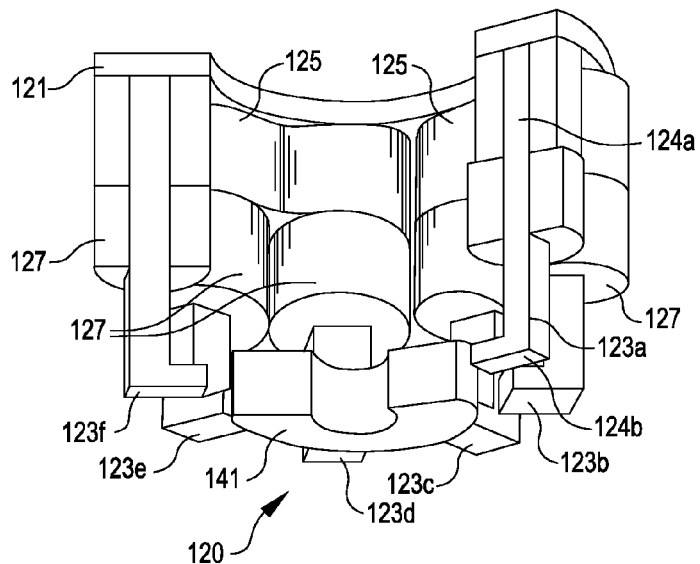
FIG. 5 is a partial cut-away perspective view of a stator of a blood pump.

With reference to FIGS. 3 to 5, a left ventricular assist blood pump assembly 100 having a circular shaped housing 110 is implanted in a patient's body with a first face 111 of the housing 110 positioned against the patient's heart H and a second face 113 of the housing 110 facing away from the heart H. The first face 111 of the housing 110 includes an inlet cannula 112 extending into the left ventricle LV of the heart H. The second face 113 of the housing 110 has a chamfered edge 114 to avoid irritating other tissue that may come into contact with the blood pump assembly 100, such as the patient's diaphragm. To construct the illustrated shape of the puck-shaped housing 110 in a compact form, a stator 120 and electronics 130 of the pump assembly 100 are positioned on the inflow side of the housing toward first face 111, and a rotor 140 of the pump assembly 100 is positioned along the second face 113. This positioning of the stator 120, electronics 130, and rotor 140 permits the edge 114 to be chamfered along the contour of the rotor 140, as illustrated in at least FIGS. 2-4, for example.

Referring to FIG. 4, the blood pump assembly 100 includes a dividing wall 115 within the housing 110 defining a blood flow conduit 103. The blood flow conduit 103 extends from an inlet opening 101 of the inlet cannula 112 through the stator 120 to an outlet opening 105 defined by the housing 110. The rotor 140 is positioned within the blood flow conduit 103. The stator 120 is disposed circumferentially about a first portion 140a of the rotor 140, for example about a permanent magnet 141. The stator 120 is also positioned relative to the rotor 140 such that, in use, blood flows within the blood flow conduit 103 through the stator 120 before reaching the rotor 140. The permanent magnet 141 has a permanent magnetic north pole N and a permanent magnetic south pole S for combined active and passive magnetic levitation of the rotor 140 and for rotation of the rotor 140. The rotor 140 also has a second portion 140b that includes impeller blades 143. The impeller blades 143 are located within a volute 107 of the blood flow conduit such that the impeller blades 143 are located proximate to the second face 113 of the housing 110.

The puck-shaped housing 110 further includes a peripheral wall 116 that extends between the first face 111 and a removable cap 118. As illustrated, the peripheral wall 116 is formed as a hollow circular cylinder having a width W between opposing portions of the peripheral wall 116. The housing 110 also has a thickness T between the first face 111 and the second face 113 that is less than the width W. The thickness T is from about 0.5 inches to about 1.5 inches, and the width W is from about 1 inch to about 4 inches. For example, the width W can be approximately 2 inches, and the thickness T can be approximately 1 inch.

The peripheral wall 116 encloses an internal compartment 117 that surrounds the dividing wall 115 and the blood flow conduit 103, with the stator 120 and the electronics 130 disposed in the internal compartment 117 about the dividing wall 115. The removable cap 118 includes the second face 113, the chamfered edge 114, and defines the outlet opening 105. The cap 118 can be engaged via threads with the peripheral wall 116 to seal the cap 118 in engagement with the peripheral wall 116. The cap 118 includes an inner surface 118a of the cap 118 that defines the volute 107 that is in fluid communication with the outlet opening 105.

Within the internal compartment 117, the electronics 130 are positioned adjacent to the first face 111 and the stator 120 is positioned adjacent to the electronics 130 on an opposite side of the electronics 130 from the first face 111. The electronics 130 include circuit boards 131 and various components carried on the circuit boards 131 to control the operation of the pump 100 (e.g., magnetic levitation and/or drive of the rotor) by controlling the electrical supply to the stator 120. The housing 110 is configured to receive the circuit boards 131 within the internal compartment 117 generally parallel to the first face 111 for efficient use of the space within the internal compartment 117. The circuit boards also extend radially-inward towards the dividing wall 115 and radially-outward towards the peripheral wall 116. For example, the internal compartment 117 is generally sized no larger than necessary to accommodate the circuit boards 131, and space for heat dissipation, material expansion, potting materials, and/or other elements used in installing the circuit boards 131. Thus, the external shape of the housing 110 proximate the first face 111 generally fits the shape of the circuits boards 131 closely to provide external dimensions that are not much greater than the dimensions of the circuit boards 131.

With continued reference to FIGS. 4 and 5, the stator 120 includes a back iron 121 and pole pieces 123a-123f arranged at intervals around the dividing wall 115. The back iron 121 extends around the dividing wall 115 and is formed as a generally flat disc of a ferromagnetic material, such as steel, in order to conduct magnetic flux. The back iron 121 is arranged beside the control electronics 130 and provides a base for the pole pieces 123a-123f.

Each of the pole piece 123a-123f is L-shaped and has a drive coil 125 for generating an electromagnetic field to rotate the rotor 140. For example, the pole piece 123a has a first leg 124a that contacts the back iron 121 and extends from the back iron 121 towards the second face 113. The pole piece 123a may also have a second leg 124b that extends from the first leg 124a through an opening of a circuit board 131 towards the dividing wall 115 proximate the location of the permanent magnet 141 of the rotor 140. In an aspect, each of the second legs 124b of the pole pieces 123a-123f is sticking through an opening of the circuit board 131. In an aspect, each of the first legs 124a of the pole pieces 123a-123f is sticking through an opening of the circuit board 131. In an aspect, the openings of the circuit board are enclosing the first legs 124a of the pole pieces 123a-123f.

In a general aspect, the implantable blood pump 100 may include a Hall sensor that may provide an output voltage, which is directly proportional to a strength of a magnetic field that is located in between at least one of the pole pieces 123a-123f and the permanent magnet 141, and the output voltage may provide feedback to the control electronics 130 of the pump 100 to determine if the rotor 140 and/or the permanent magnet 141 is not at its intended position for the operation of the pump 100. For example, a position of the rotor 140 and/or the permanent magnet 141 may be adjusted, e.g., the rotor 140 or the permanent magnet 141 may be pushed or pulled towards a center of the blood flow conduit 103 or towards a center of the stator 120.

Each of the pole pieces 123a-123f also has a levitation coil 127 for generating an electromagnetic field to control the radial position of the rotor 140. Each of the drive coils 125 and the levitation coils 127 includes multiple windings of a conductor around the pole pieces 123a-123f. Particularly, each of the drive coils 125 is wound around two adjacent ones of the pole pieces 123, such as pole pieces 123d and 123e, and each levitation coil 127 is wound around a single pole piece. The drive coils 125 and the levitation coils 127 are wound around the first legs of the pole pieces 123, and magnetic flux generated by passing electrical current though the coils 125 and 127 during use is conducted through the first legs and the second legs of the pole pieces 123 and the back iron 121. The drive coils 125 and the levitation coils 127 of the stator 120 are arranged in opposing pairs and are controlled to drive the rotor and to radially levitate the rotor 140 by generating electromagnetic fields that interact with the permanent magnetic poles S and N of the permanent magnet 141. Because the stator 120 includes both the drive coils 125 and the levitation coils 127, only a single stator is needed to levitate the rotor 140 using only passive and active magnetic forces. The permanent magnet 141 in this configuration has only one magnetic moment and is formed from a monolithic permanent magnetic body 141. For example, the stator 120 can be controlled as discussed in U.S. Pat. No. 6,351,048, the entire contents of which are incorporated herein by reference for all purposes. The control electronics 130 and the stator 120 receive electrical power from a remote power supply via a cable 119 (FIG. 3). Further related patents, namely U.S. Pat. Nos. 5,708,346, 6,053,705, 6,100,618, 6,222,290, 6,249,067, 6,278,251, 6,351,048, 6,355,998, 6,634,224, 6,879,074, and 7,112,903, all of which are incorporated herein by reference for all purposes in their entirety.

The rotor 140 is arranged within the housing 110 such that its permanent magnet 141 is located upstream of impeller blades in a location closer to the inlet opening 101. The permanent magnet 141 is received within the blood flow conduit 103 proximate the second legs 124b of the pole pieces 123 to provide the passive axial centering force though interaction of the permanent magnet 141 and ferromagnetic material of the pole pieces 123. The permanent magnet 141 of the rotor 140 and the dividing wall 115 form a gap 108 between the permanent magnet 141 and the dividing wall 115 when the rotor 140 is centered within the dividing wall 115. The gap 108 may be from about 0.2 millimeters to about 2 millimeters. For example, the gap 108 is approximately 1 millimeter. The north permanent magnetic pole N and the south permanent magnetic pole S of the permanent magnet 141 provide a permanent magnetic attractive force between the rotor 140 and the stator 120 that acts as a passive axial centering force that tends to maintain the rotor 140 generally centered within the stator 120 and tends to resist the rotor 140 from moving towards the first face 111 or towards the second face 113. When the gap 108 is smaller, the magnetic attractive force between the permanent magnet 141 and the stator 120 is greater, and the gap 108 is sized to allow the permanent magnet 141 to provide the passive magnetic axial centering force having a magnitude that is adequate to limit the rotor 140 from contacting the dividing wall 115 or the inner surface 118a of the cap 118. The rotor 140 also includes a shroud 145 that covers the ends of the impeller blades 143 facing the second face 113 that assists in directing blood flow into the volute 107. The shroud 145 and the inner surface 118a of the cap 118 form a gap 109 between the shroud 145 and the inner surface 118a when the rotor 140 is levitated by the stator 120. The gap 109 is from about 0.2 millimeters to about 2 millimeters. For example, the gap 109 is approximately 1 millimeter.

As blood flows through the blood flow conduit 103, blood flows through a central aperture 141a formed through the permanent magnet 141. Blood also flows through the gap 108 between the rotor 140 and the dividing wall 115 and through the gap 109 between the shroud 145 and the inner surface 108a of the cap 118. The gaps 108 and 109 are large enough to allow adequate blood flow to limit clot formation that may occur if the blood is allowed to become stagnant. The gaps 108 and 109 are also large enough to limit pressure forces on the blood cells such that the blood is not damaged when flowing through the pump 100. As a result of the size of the gaps 108 and 109 limiting pressure forces on the blood cells, the gaps 108 and 109 are too large to provide a meaningful hydrodynamic suspension effect. That is to say, the blood does not act as a bearing within the gaps 108 and 109, and the rotor is only magnetically-levitated. In various embodiments, the gaps 108 and 109 are sized and dimensioned so the blood flowing through the gaps forms a film that provides a hydrodynamic suspension effect. In this manner, the rotor can be suspended by magnetic forces, hydrodynamic forces, or both.

Because the rotor 140 is radially suspended by active control of the levitation coils 127 as discussed above, and because the rotor 140 is axially suspended by passive interaction of the permanent magnet 141 and the stator 120, no rotor levitation components are needed proximate the second face 113. The incorporation of all the components for rotor levitation in the stator 120 (i.e., the levitation coils 127 and the pole pieces 123) allows the cap 118 to be contoured to the shape of the impeller blades 143 and the volute 107. Additionally, incorporation of all the rotor levitation components in the stator 120 eliminates the need for electrical connectors extending from the compartment 117 to the cap 118, which allows the cap to be easily installed and/or removed and eliminates potential sources of pump failure.

In use, the drive coils 125 of the stator 120 generates electromagnetic fields through the pole pieces 123 that selectively attract and repel the magnetic north pole N and the magnetic south pole S of the rotor 140 to cause the rotor 140 to rotate within stator 120. For example, the Hall sensor may sense a current position of the rotor 140 and/or the permanent magnet 141, wherein the output voltage of the Hall sensor may be used to selectively attract and repel the magnetic north pole N and the magnetic south pole S of the rotor 140 to cause the rotor 140 to rotate within stator 120. As the rotor 140 rotates, the impeller blades 143 force blood into the volute 107 such that blood is forced out of the outlet opening 105. Additionally, the rotor draws blood into pump 100 through the inlet opening 101. As blood is drawn into the blood pump by rotation of the impeller blades 143 of the rotor 140, the blood flows through the inlet opening 101 and flows through the control electronics 130 and the stator 120 toward the rotor 140. Blood flows through the aperture 141a of the permanent magnet 141 and between the impeller blades 143, the shroud 145, and the permanent magnet 141, and into the volute 107. Blood also flows around the rotor 140, through the gap 108 and through the gap 109 between the shroud 145 and the inner surface 118a of the cap 118. The blood exits the volute 107 through the outlet opening 105, which may be coupled to an outflow cannula.

Figure 6:
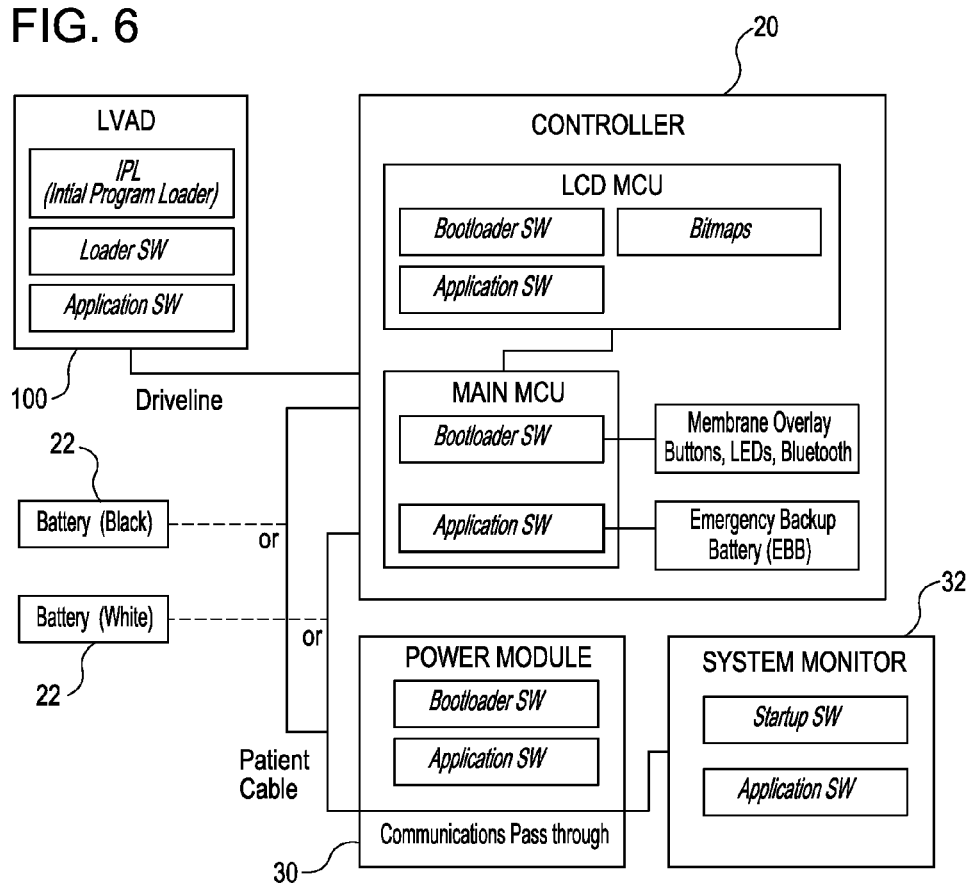
FIG. 6 is a schematic diagram of an overall communication architecture of the mechanical support system of FIG. 1.

FIG. 6 is a schematic diagram of an overall communication architecture of the mechanical support system of FIG. 1. A driveline couples the implanted blood pump assembly 100 to the external system controller 20, which monitors system operation via various software applications. The blood pump assembly 100 itself also includes several software applications that are executable by the on board electronics 130 (e.g., processors) for various functions, such as to control radial levitation and/or drive of the rotor of the pump assembly 100 during operation. The external system controller 20 may in turn be coupled to batteries 22 or a power module 30 that connect to an AC electrical outlet. The external system controller 20 may also include an emergency backup battery (EBB) to power the system (e.g., when the batteries 22 are depleted) and a membrane overlay, including Bluetooth capabilities for wireless data communication. An external computer having a system monitor 32 that is configurable by an operator, such as clinician or patient, may further be coupled to the circulatory support system for configuring the external system controller 20, implanted blood pump assembly 100, and/or patient specific parameters, updating software on the external system controller 20 and/or implanted blood pump assembly 100, monitoring system operation, and/or as a conduit for system inputs or outputs.

Onboard Storage of Patient Specific Parameters

In many embodiments, the on board electronics 130 of the blood pump assembly 100 stores patient specific parameters that are used by the electronics 130 to control patient specific operational aspects of the blood pump assembly 100. FIG. 7 shows a simplified schematic drawing of an embodiment of the electronics 130. As described above, the electronics 130 include the circuit boards 131. In many embodiments, the circuit boards 131 include one or more processors 132 and a memory device 133 operatively coupled to the one or more processors 132. The memory device 133 can include any suitable forms of memory, for example, a read only memory (ROM) 134 and a random access memory (RAM) 135. The ROM 134 can be used to store basic instructional sets for the operation of the one or more processors 132. The RAM 135, or any other suitable memory device such as long term, short term, volatile, nonvolatile, or other suitable storage medium, can be used to store the patient specific parameters that are used by the electronics 130 to control patient specific operational aspects of the blood pump assembly 100, as well as related software modules.

FIG. 8 shows a set of patient specific parameters that can be stored in the on board electronics 130 and used by the electronics 130 to control operational aspects of the blood pump assembly 100. Such patient specific parameters can include, but are not limited to, one or more of the following: (a) a patient specific set speed for the blood pump assembly 100; (b) a patient specific low speed limit for the blood pump assembly 100; (c) a patient specific operational mode for the blood pump assembly 100; (d) a patient specific hematocrit value; (e) a patient specific hematocrit date; (f) a patient specific blood density; (g) a patient specific periodic log rate for event and periodic data; and (h) a patient specific spoken language. As described below, the patient specific set speed and low speed limit can be employed to determine an operational target speed for the blood pump for various operational scenarios. In many embodiments, the patient specific blood pump operational mode parameter can be set to designate either continuous mode or pulse mode. In pulse mode, the blood pump is operated at a varying rate so that the resulting blood flow in the patient has a pulse similar to that naturally produced when blood is pumped via a normally functioning heart. In contrast, in continuous mode, the blood pump operational rate is not substantially varied, at least not so as to cause the patient to have a pulse. Instead, in continuous mode, the blood pump operational rate is more uniform or steady state, but may still change over time as suitable in view of changing operational scenarios. The patient specific hematocrit value represents the percentage of a volume of the patient's blood that is made up of red blood cells. The patient specific hematocrit date indicates the date on which the patient's hematocrit value was measured. The patient specific period log rate for event and periodic data can be used by the electronics 130 to determine how often to record data with respect to patient parameters measured by the mechanical circulatory support system 10. The patient specific spoken language can be used to ensure that the external system controller 20 displays messages and instructions to the patient in a language that is understood by the patient.

FIG. 9 illustrates a normal operational mode data flow of the patient specific settings within the mechanical circulatory support system 10. To ensure that a single authoritative source of the patient specific settings is employed, the patient specific settings stored within the electronics 130 are transmitted to external system controller 20 for use in program modules executed therein. To avoid potentially conflicting data, the external system controller 20 is configured to rely solely on the patient specific settings that are transmitted from the electronics 130. For example, instead of relying on one or more values of patient specific settings stored within the external system controller 20, the external controller 20 can transmit a data request 136 to the on board electronics 130 for one or more of the patient specific parameters stored in the electronics 130. In response, the electronics 130 makes a transmission 137 to communicate the requested data to the external controller 20. Accordingly, it is assured that the patient specific settings employed in processes accomplished by the external controller 20 match those stored within the electronics 130.

FIG. 10 illustrates a process by which a health care professional can change the patient specific settings stored in the electronics 130. As describe above and illustrated in FIG. 6, the system monitor 32 can be coupled with the external system controller 20 and employed to configure the implanted blood pump assembly 100. For example, the system monitor 32 can transmit a data request 151 to the external system controller 20 for one or more of the patient specific settings stored in the electronics 130. The system monitor 32 responds by transmitting a similar data request 152 to the electronics 130. In response, the electronics 130 makes a data transmission 153 to the external controller 20 that includes the requested data. The external controller then makes a transmission 154 to the system monitor 32 that communicates the requested patient specific setting data to the system monitor 32. Upon review of the patient specific settings currently stored in the electronics 130, any desired changes can then be made. For example, the system monitor 32 can transmit a change command 155 that designates which patient specific setting(s) to change as well as the value to which the setting(s) is to be changed. In response, the controller 20 transmits a similar change command 156 to the electronics 130, which then stores the new patient specific setting(s). For verification purposes, the electronics 130 can make a data transmission to the controller 20 that includes the changed patient specific setting(s), which can then be forwarded by the controller 20 to the system monitor 32 via transmission 158 for display and verification.

The patient specific settings can be used in conjunction with event based rules to control the operational speed of the implanted blood pump assembly 100. In many embodiments, the external system controller 20 operates the blood pump at a target speed that is based on the patient specific set speed, the patient specific low speed limit, and a set of event based rules for the target speed. FIG. 11 shows events that can be assessed as part of event based rules for the target speed. For example, the target speed can be set to zero if the target running mode for the blood pump is set as stopped. The target speed can be set to the lower of the patient low speed limit and the patient set speed if the blood pump has just started up. The target speed can be reduced to the patient low speed limit if a suction event, as detected by the pump assembly 100, is occurring. The target speed can be reduced to the patient low speed limit if rotor instability is occurring. The target speed can be reduced to the patient low speed limit if a critical power hazard has been active for more than a predetermined amount of time (e.g., for greater and equal to 15 minutes). The target speed can be reduced to the patient low speed limit if the pump assembly 100 is running on emergency backup battery power and the backup battery voltage is less than a predetermined value (e.g., less than or equal to 10.4 volts). The target speed can be maintained at the patient set speed if the patient set speed is less than the patient low speed limit. Otherwise, in the absence of the above-described events, the target speed can be set to the patient set speed.

The patient specific settings can be used in conjunction with event based rules to control the operational mode of the implanted blood pump assembly 100. In many embodiments, the external system controller 20 operates the blood pump in a target operational mode that is based on the patient specific operating mode of the blood pump and a set of event based rules for the target operating mode. FIG. 12 shows events that can be assessed as part of event based rules for the target operating mode. For example, the target operating mode can be set to continuous if the target running mode for the blood pump is set as stopped. The target operating mode can be set to continuous if the current speed of the blood pump is less than an auto start threshold speed. The target operating mode can be set to continuous if the blood pump assembly is running on emergency backup battery power. The target operating mode can be set to continuous if a critical power hazard is active. Otherwise, in the absence of the above-described events, the target operating mode can be set to the patient operating mode.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A blood pump assembly, comprising:
   an implantable blood pump configured to supplement or replace a pumping function of a heart;
   an implantable control unit communicatively coupled with the blood pump and storing preprogrammed patient specific settings on which control of the implantable blood pump is based; and
   a non-implanted external control unit configured to be operatively coupled with the implantable blood pump and to control operation of the implantable blood pump based at least in part on at least one of the preprogrammed patient specific settings communicated to the external control unit by the implantable control unit.

2. The pump assembly of claim 1, wherein the preprogrammed patient specific settings include a patient specific operating mode of the blood pump.

3. The pump assembly of claim 2, wherein the patient specific operating mode for the blood pump can be selected to be continuous or pulsatile.

4. The pump assembly of claim 3, wherein the external control unit controls the blood pump to run in a target operating mode selected as either the patient specific operating mode or continuous.

5. The pump assembly of claim 1, wherein the preprogrammed patient specific settings include a patient specific set speed of the blood pump.

6. The pump assembly of claim 1, wherein the preprogrammed patient specific settings include a patient specific low speed limit for the blood pump.

7. The pump assembly of claim 1, wherein the preprogrammed patient specific settings include at least one of a patient specific hematocrit and a patient specific hematocrit date.

8. The pump assembly of claim 1, wherein the preprogrammed patient specific settings include a patient specific blood density.

9. The pump assembly of claim 1, wherein the preprogrammed patient specific settings include a patient specific periodic log rate for event and periodic data.

10. The pump assembly of claim 1, wherein the preprogrammed patient specific settings include a patient specific spoken language.

11. The pump assembly of claim 1, wherein one or more of the preprogrammed patient specific settings stored within the implantable control unit can be selectively changed or updated while the implantable control unit remains implanted.

12. The pump assembly of claim 11, wherein the preprogrammed patient specific settings stored within the implantable control unit can be changed via wireless communication.

13. The pump assembly of claim 1, wherein a plurality of the preprogrammed patient specific settings stored within the implantable control unit are communicated to the external control unit by the implantable control unit for use by the external control unit in controlling operation of the blood pump.

14. The pump assembly of claim 1, further comprising a hard wire driveline operatively coupling the external control unit and the implantable blood pump, the hard wire drive line being configured to provide operating power to the implantable blood pump.

15. The pump assembly of claim 1, further comprising a transcutaneous energy transfer system configured to wirelessly provide operating power to the implantable blood pump.

16. The pump assembly of claim 1, wherein the external control unit is configured to control the blood pump to run at a target speed.

17. The pump assembly of claim 16, wherein the target speed is based at least in part on at least one of a patient specific low speed limit of the blood pump and a patient specific set speed limit of the blood pump.

18. The pump assembly of claim 1, wherein the implantable control unit is integrally housed with the blood pump.

19. The pump assembly of claim 1, wherein the implantable control unit is configured to transmit one or more of the preprogrammed patient specific settings stored on the implantable control unit to the external control unit in response to a data request transmitted by the external control unit to the implantable control unit.

20. The pump assembly of claim 1, wherein:
the preprogrammed patient specific settings include a patient specific operating mode of the blood pump; and
the implantable control unit is configured to transmit the patient specific operating mode to the external control unit in response to a data request transmitted by the external control unit to the implantable control unit.

21. The pump assembly of claim 1, wherein the preprogrammed patient specific settings include one or more of: (a) a patient specific set speed of the blood pump, (b) a patient specific low speed limit for the blood pump, (c) at least one of a patient specific hematocrit and a patient specific hematocrit date, (d) a patient specific blood density, (e) a patient specific periodic log rate for event and periodic data, and (f) a patient specific spoken language.

22. A blood pump assembly, comprising:
an implantable blood pump configured to supplement or replace a pumping function of a heart;
an implantable control unit communicatively coupled with the blood pump and storing preprogrammed patient specific settings on which control of the implantable blood pump is based, the preprogrammed patient specific settings including one or more of: (a) a patient specific set speed of the blood pump, (b) a patient specific low speed limit for the blood pump, (c) at least one of a patient specific hematocrit and a patient specific hematocrit date, (d) a patient specific blood density, (e) a patient specific periodic log rate for event and periodic data, and (f) a patient specific spoken language; and
a non-implanted external control unit configured to be operatively coupled with the implantable blood pump and to control operation of the implantable blood pump based at least in part on at least one of the preprogrammed patient specific settings communicated to the external control unit by the implantable control unit;
wherein the implantable control unit is configured to transmit the preprogrammed patient specific settings to the external control unit in response to a data request transmitted by the external control unit to the implantable control unit.

23. The pump assembly of claim 22, wherein the preprogrammed patient specific settings include a patient specific operating mode of the blood pump.

24. The pump assembly of claim 23, wherein the patient specific operating mode for the blood pump can be selected to be continuous or pulsatile.

25. The pump assembly of claim 24, wherein the external control unit controls the blood pump to run in a target operating mode selected as either the patient specific operating mode or continuous.

26. The pump assembly of claim 22, wherein the implantable control unit is integrally housed with the blood pump.

* * * * *